United States Patent [19]

Zadgorska et al.

[11] Patent Number: 5,315,369
[45] Date of Patent: May 24, 1994

[54] METHOD OF AND APPARATUS FOR FEEDING A SAMPLE TO A PLASMA OF AN INDUCTIVELY COUPLED PLASMA ATOMIC EMISSION SPECTROMETER

[75] Inventors: Zdravka Zadgorska; Hubertus Nickel, both of Jülich, Fed. Rep. of Germany

[73] Assignee: Forschungszentrum Julich GmbH, Julich, Fed. Rep. of Germany

[21] Appl. No.: 963,579

[22] Filed: Oct. 19, 1992

[30] Foreign Application Priority Data

Oct. 18, 1991 [DE] Fed. Rep. of Germany ....... 4134512

[51] Int. Cl.$^5$ ............................................. G01N 21/73
[52] U.S. Cl. ..................................... 356/316; 356/315
[58] Field of Search ................................ 356/315, 316

[56] References Cited

U.S. PATENT DOCUMENTS 5,066,125 11/1991 Rogers et al. ........................ 356/316

FOREIGN PATENT DOCUMENTS 3424696 6/1986 Fed. Rep. of Germany .

OTHER PUBLICATIONS

Thermal Vaporisation for Inductively Coupled Plasma Optical Emission Spectrometry; vol. 1, Jun. 1986, pp. 171–184.

Primary Examiner—Vincent P. McGraw
Attorney, Agent, or Firm—Herbert Dubno

[57] ABSTRACT

A sample is fed to an ICP-AES by applying suction to a mouth of the sample vessel extending into the central or inner capillary tube of the burner from an annular orifice or a plurality of spaced apart orifices. The amount of sample material is controlled by volume flow control or gas pressure control. The sample is in the form of a powder or vapor without dilution or entrainment of chemical contaminants.

20 Claims, 3 Drawing Sheets

METHOD OF AND APPARATUS FOR FEEDING A SAMPLE TO A PLASMA OF AN INDUCTIVELY COUPLED PLASMA ATOMIC EMISSION SPECTROMETER

FIELD OF THE INVENTION

Our present invention relates to a method of and to an apparatus or device for feeding a sample to be analyzed to a plasma of an inductively coupled plasma (ICP) atomic emission spectrometer (AES). More particularly, the invention relates to the feeding of a sample to an ICP-AES whereby sample loss is minimized, dilution of a sample with possible contaminants is precluded, and solid or molten samples can be employed.

BACKGROUND OF THE INVENTION

Atomic emission spectrometer (AES) with inductively coupled plasma (ICP) provides the advantage over classical AES that solid pulverulent samples can be introduced into the plasma without the incorporation in the samples of possible chemical contaminants required in the earlier systems to solubilize or dispense the samples. Since solvents and chemicals required for preparing the samples can be eliminated and the expense and time consuming operations for sample preparation avoided, ICP-AES represents a significant advantage. It is also advantageous over classical AES that the reduction in sensitivity resulting from dilution of the sample is precluded as well.

In spite of these advantages, however, the use of a sample feed to the ICP plasma without dilution and contamination by chemicals used to process the sample has not found widespread application, since sample loss has not been possible to avoid in earlier systems A mechanical lifting of the sample containing crucible or graphite vessel is described in Applied Spectroscopy, Vol. 40, No. 3, 1986, pages 387 ff.

In this system, the sample-containing vessel, i.e. a graphite crucible, is lifted toward the plasma torch. The elevation of the crucible has been found, however, to disturb the plasma and there is also a danger of carbide formation from the plasma materials within the hot plasma from the carbon of the crucible. This can reduce the resolution of the system.

In a literature survey or report entitled "Thermal Vaporisation for Inductively Coupled Plasma Optical Emission Spectrometry" authored by Matusiewicz, June 1986, Vol. 1, the importance of the feed systems and the interface between the sample source and the plasma are discussed, although a satisfactory solution to the problems described has not been there taught.

OBJECTS OF THE INVENTION

It is, therefore, the principal object of the invention to provide an improved process or method of feeding sample material to a plasma which avoids the aforedescribed drawbacks and feeds the sample without dilution or chemical contamination and without loss to the plasma burner or torch in ICP-AES.

Another object of the invention is to provide a method of feeding a sample to an ICP-AES plasma which utilizes a relatively simple system without complex mechanisms and mechanically movable crucibles or the like.

Still another object of our invention is to provide an improved apparatus or device for feeding such samples to an ICP-AES so as to minimize losses, ensure high resolution and high analytical efficiency.

SUMMARY OF THE INVENTION

These objects and others which will become apparent hereinafter are attained, in accordance with the invention by providing a mouth for a sample vessel which opens directly within the inner capillary or central tube of a plasma burner for an ICP-AES and around which a gas stream can be generated so that the gas stream forms a sheath surrounding the axis of the capillary tube, the sample is drawn through the mouth at least in part by suction of the gas stream flowing past the mouth, and the pulverulent or molten sample is drawn upwardly or is transformed into the vapor state at least in part by this suction and, as it is moved upwardly, is metered into the plasma.

The sheathing gas, which preferably is argon, flows from the gas feeder into the central tube through at least one nozzle or passage, e.g. an annular nozzle or an array of axially extending passages so that the gas flow is rectilinear from a location upstream of the mouth to a location downstream thereof along the capillary tube, the nozzle generating an increased velocity in the capillary tube.

The velocity increase depends, of course, upon the volume or throughput of the gas and the cross section of the passage or passages in accordance with the Bernonlli principle.

The increased gas velocity, moreover, generates the suction at the mouth which is responsible for transformation of the sample material, which can be at least in part in a molten state, into a vapor, or can entrain the pulverulent material directly from the sample vessel into the plasma.

The amount of entrained sample can be controlled by adjusting the gas pressure and/or the gas throughput or volume rate of flow. With the method of the invention, the sample material can be delivered to the plasma without contamination and, because of the sheath formed by the gas around the sample, deposition of sample material on the inner wall of the central tube can be avoided, thereby precluding loss of sample material in this manner.

A closed system can be provided whereby the tube is sealed to a housing forming the passage or passages surrounding a tubular formation forming the mouth and beneath which the sample holder is provided. The opening or openings of the single annular passage or the multiplicity of axial passages can lie in the same plane as the mouth of the sample vessel. The annular configuration of the passage is preferred to insure the formation of the gas sheath.

More particularly, the improved method of feeding a sample to an inductively coupled plasma atomic emission spectrometer torch or burner can comprise the steps of:

(a) connecting a sample-containing vessel to an upright central capillary tube of an inductively coupled plasma atomic emission spectrometer plasma torch so that an upwardly open mouth of the vessel communicates directly and extends into the tube while defining an all-around clearance around the mouth with the tube;

(b) feeding a gas stream from below into the clearance to generate a rising flow of the gas around the mouth and along the tube in a sheath around an axis of the tube;

(c) generating with the gas stream in the vessel by passage of the flow past the mouth, a suction inducing a sample contained in the vessel to flow upwardly along the axis within the sheath in the tube; and (d) entraining the sample with the gas into the plasma to meter the sample into the plasma.

In apparatus respects, the sample feeder can comprise:

an upright central tube forming an inner capillary for an inductively coupled plasma atomic, emission spectrometer torch;

means for connecting a sample-containing vessel to the upright central capillary tube of the inductively coupled plasma atomic emission spectrometer plasma torch so that an upwardly open mouth of the vessel communicates directly and extends into the tube while defining a all-around clearance around the mouth with the tube; and means for feeding a gas stream from below into the clearance to generate a rising flow of the gas around the mouth and along the tube in a sheath around an axis of the tube, thereby generating with the gas stream in the vessel by passage of the flow past the mouth, a suction inducing a sample contained in the vessel to flow upwardly along the axis within the sheath in the tube and entraining the sample with the gas into the plasma to meter the sample into the plasma.

Alternatively, the apparatus can comprise:
an upright central tube forming an inner capillary for an inductively coupled plasma atomic emission spectrometer torch;

means for connecting a sample-containing vessel to the upright central capillary tube of the inductively coupled plasma atomic emission spectrometer plasma torch so that an upwardly open mouth of the vessel communicates directly and extends into the tube while defining at least one rectilinear passage extending from a location upstream of the mouth to a location at the mouth for discharging gas into the tube substantially all around the mouth; and means for feeding a gas stream from below into the passage to generate a rising flow of the gas around the mouth and along the tube in a sheath around an axis of the tube, thereby generating with the gas stream in the vessel by passage of the flow past the mouth, a suction inducing a sample contained in the vessel to flow upwardly along the axis within the sheath in the tube and entraining the sample with the gas into the plasma to meter the sample into the plasma.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
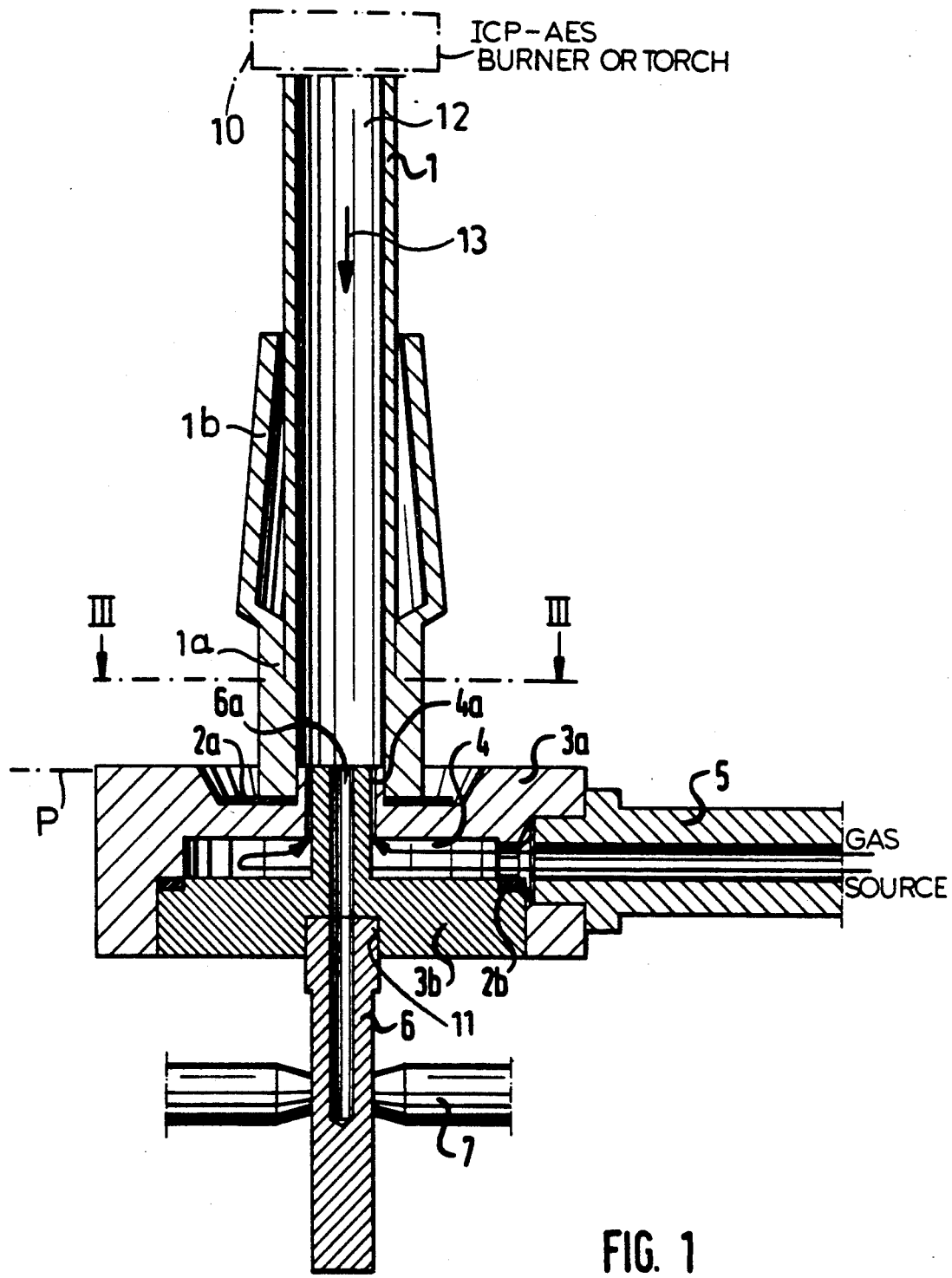
FIG. 1 is an axial cross sectional view through the apparatus of the invention showing a graphite crucible as the sample holder.
Figure 2:
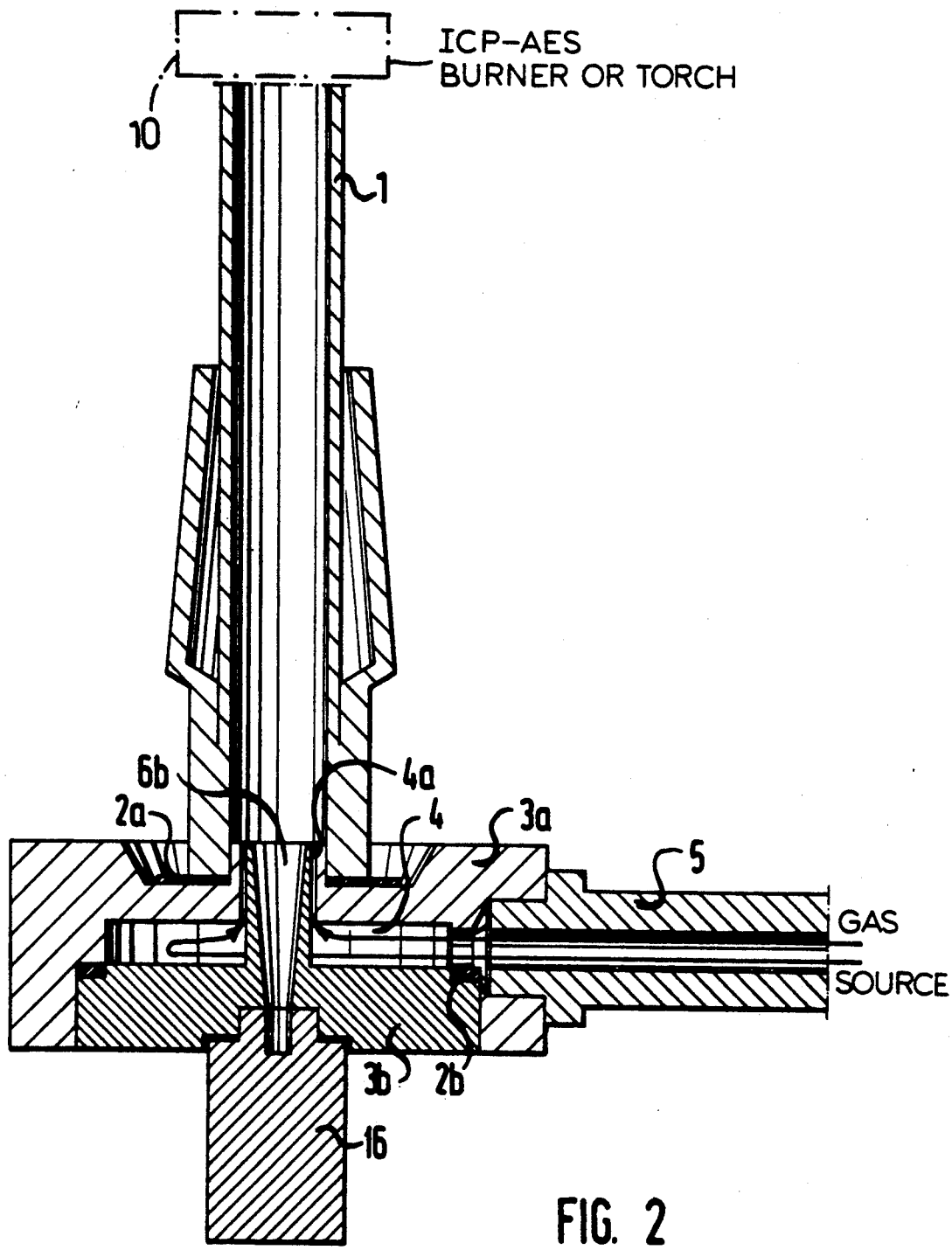
FIG. 2 is a similar view of an embodiment which utilizes an unheated sample holder.
Figure 3:
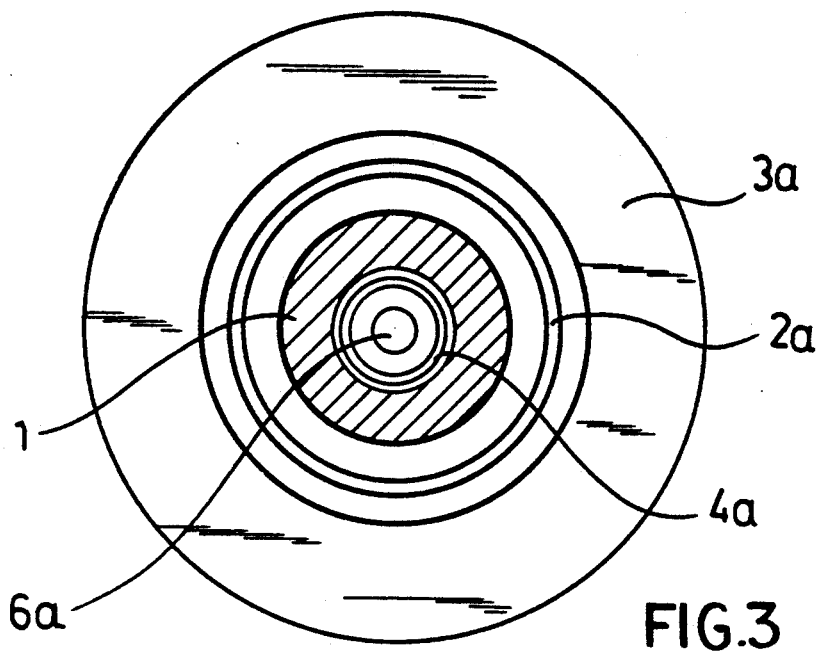
FIG. 3 is a cross sectional view taken along the line III—III of FIG. 1 with the ga supplied tube detached.

As is expressly clear from FIGS. 1 to 3, a sample feeder supplying an ICP-AES burner or torch 10 can comprise an inner capillary tube 1 having an extension 1a forming an apron 1b reaching up around the lower portion of the tube 1.

This tube is sealed via a sealing washer 2a to a housing 3a or a sample feed system formed by the parts 3a, 3b which are joined with an annular seal 2b between them.

The parts 3a, 3b define a plenum chamber 4 around a tubular formation 6a forming an extension of the interior of the sample holder or vessel 6 which here is a graphite crucible (FIG. 1) affixed in a socket 11 at the side of the part 3b opposite that from which the tubular formation 6a extends upwardly.

The crucible 6 can be heated between electrode 7 to at least partially melt the contents of the crucible, namely, the sample.

From the plenum 4, the housing 3a forms around the tubular formation 6a, an annular nozzle 4 which extends rectilinearly from a location beyond the mouth defined by the tubular formation 6a, to the plane of the mouth at which the passage 4a opens. This plane is represented at P in FIG. 1.

Argon fed by a delivery tube 5 to the plenum 4 then passes upwardly through the annular passage 4a as represented by the arrows to form the sheath 12 around the sample stream 13 arising along the axis of the tube 1 in the form of a vapor produced at least in part by the suction effect at the mouth of the high velocity gas forming the sheath. The sample is thus entrained into the plasma of the torch or burner 10.

As can be seen from FIG. 2, a vessel 16 can supply pulverulent material if an unheated sample holder is desired.

The tubular formation in this embodiment is formed with an upwardly convergent frustoconical passage 6b.

Figure 4:
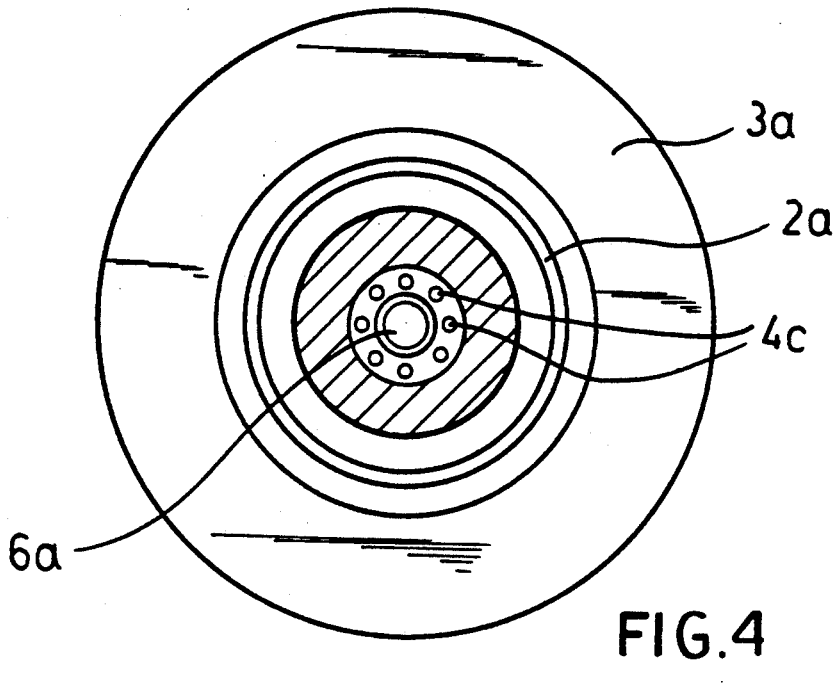
FIG. 4 is a view similar to FIG. 3 but wherein the annular gas passage has been replaced by an array of equispaced passages or orifices.

As a comparison of FIGS. 3 and 4 will show, the annular passage 4a of FIGS. 1 and 2 can be replaced by a plurality of equispaced rectilinear bores 4c also at the plane of the mouth to deliver the gas to the tube all around the mouth.

We claim:

1. A method of feeding sample material to a plasma of an inductively coupled plasma atomic emission spectrometer, comprising the steps of:
    (a) connecting a sample-containing vessel to an upright central capillary tube of an inductively coupled plasma atomic emission spectrometer plasma torch so that an upwardly open mouth of said vessel communicates directly and extends into said tube while defining an all-around clearance around said mouth with said tube;
    (b) feeding a gas stream from below into said clearance to generate a rising flow of the gas around said mouth and along said tube in a sheath around an axis of the tube;
    (c) generating with said gas stream in said vessel by passage of said flow past said mouth, a suction inducing a sample contained in said vessel to flow upwardly along said axis within said sheath in said tube; and (d) entraining said sample with said gas into said plasma to meter said sample into said plasma.

2. The method defined in claim 1, further comprising the step of controlling an amount of said sample entrained with said gas by regulating a pressure of said gas.

3. The method defined in claim 1, further comprising the step of controlling an amount of said sample entrained with said gas by regulating a throughput of said gas.

4. The method defined in claim 1, further comprising the step of controlling an amount of said sample entrained with said gas by regulating both a pressure and a throughput of said gas.

5. The method defined in claim 1 wherein said gas is conducted from a region upstream of said mouth and along said tube downstream of said mouth rectilinearly.

6. The method defined in claim 1 wherein said sample is a pulverulent solid sample, further comprising the step of melting said sample.

7. The method defined in claim 1, further comprising the step of heating said sample to at least partly vaporize said sample.

8. The method defined in claim 1 wherein said gas stream is admitted to a gas plenum of a greater diameter than that of said clearance and communicating with said clearance below a tubular formation forming said mouth at an upper end thereof.

9. A sample feeder for an inductively coupled plasma atomic emission spectrometer, comprising:
an upright central tube forming an inner capillary for an inductively coupled plasma atomic emission spectrometer torch;
means for connecting a sample-containing vessel to said upright central capillary tube of said inductively coupled plasma atomic emission spectrometer plasma torch so that an upwardly open mouth of said vessel communicates directly and extends into said tube while defining an all-around clearance around said mouth with said tube; and
means for feeding a gas stream from below into said clearance to generate a rising flow of the gas around said mouth and along said tube in a sheath around an axis of the tube, thereby generating with said gas stream in said vessel by passage of said flow past said mouth, a suction inducing a sample contained in said vessel to flow upwardly along said axis within said sheath in said tube and entraining said sample with said gas into said plasma to meter said sample into said plasma.

10. The feeder defined in claim 9 wherein said means for connecting includes:
a gas guide having an upwardly extending tubular formation projecting into said tube; and
means for coupling said vessel to said gas guide on an underside thereof.

11. The feeder defined in claim 10 wherein said means for connecting further includes:
a housing receiving said gas guide and defining a gas plenum around said tubular formation and connectable with a source of said gas; and
respective seals between said gas guide and said housing and between said tube and said housing.

12. The feeder defined in claim 11 wherein said mouth and said clearance terminate in a common plane within said tube.

13. The feeder defined in claim 12, further comprising means for heating said vessel to generate said vapor.

14. A sample feeder for an inductively coupled plasma atomic emission spectrometer, comprising:
an upright central tube forming an inner capillary for an inductively coupled plasma atomic emission spectrometer torch;
means for connecting a sample-containing vessel to said upright central capillary tube of said inductively coupled plasma atomic emission spectrometer plasma torch so that an upwardly open mouth of said vessel communicates directly and extends into said tube while defining at least one rectilinear passage extending from a location upstream of said mouth to a location at said mouth for discharging gas into said tube substantially all around said mouth; and
means for feeding a gas stream from below into said passage to generate a rising flow of the gas around said mouth and along said tube in a sheath around an axis of the tube, thereby generating with said gas stream in said vessel by passage of said flow past said mouth, a suction inducing a sample contained in said vessel to flow upwardly along said axis within said sheath in said tube and entraining said sample with said gas into said plasma to meter said sample into said plasma.

15. The feeder defined in claim 14 wherein said passage is an all-around annular clearance surrounding said mouth.

16. The feeder defined in claim 14 wherein said passage is one of a multiplicity of passages spaced uniformly around said mouth.

17. The feeder defined in claim 14 wherein said means for connecting includes:
a gas guide having an upwardly extending tubular formation projecting into said tube; and
means for coupling said vessel to said gas guide on an underside thereof.

18. The feeder defined in claim 17 wherein said means for connecting further includes:
a housing receiving said gas guide and defining a gas plenum around said tubular formation and connectable with a source of said gas; and
respective seals between said gas guide and said housing and between said tube and said housing.

19. The feeder defined in claim 14 wherein said mouth and said passage terminate in a common plane within said tube.

20. The feeder defined in claim 19, further comprising means for heating said vessel to generate said vapor.

* * * * *